(12) United States Patent
Finger

(10) Patent No.: US 6,419,698 B1
(45) Date of Patent: Jul. 16, 2002

(54) ORBITAL IMPLANT DEVICE

(76) Inventor: Paul T. Finger, 1 Gracie Ter. Apt. 12A, New York, NY (US) 10028

( * ) Notice: Subject to any disclaimer, the term of this patent is extended or adjusted under 35 U.S.C. 154(b) by 0 days.

(21) Appl. No.: 09/541,283

(22) Filed: Apr. 3, 2000

(51) Int. Cl.[7] ................................................. A61F 2/14
(52) U.S. Cl. ..................................... 623/6.64; 623/6.41
(58) Field of Search .................. 623/4.1, 6.64, 623/FOR 103; 446/389, 392

(56) References Cited

U.S. PATENT DOCUMENTS

| | | | | |
|---|---|---|---|---|
| 2,653,327 A | * | 9/1953 | Allen et al. ................... | 623/4.1 |
| 3,364,501 A | * | 1/1968 | Stafford ..................... | 623/6.64 |
| 4,710,194 A | * | 12/1987 | Kelman ........................ | 623/6 |
| 4,731,077 A | * | 3/1988 | Allen .......................... | 623/4 |
| 4,902,293 A | * | 2/1990 | Feaster ........................ | 623/6 |
| 5,330,529 A | * | 7/1994 | Cepela ......................... | 623/4 |

FOREIGN PATENT DOCUMENTS

| | | | | |
|---|---|---|---|---|
| SU | 1378838 | * | 3/1988 | ........ 623/FOR 103 |

* cited by examiner

*Primary Examiner*—Paul Prebilic
*Assistant Examiner*—Will H Matthews

(57) ABSTRACT

An orbital implant device is provided. The orbital implant device comprises a frame, defining a plurality of openings, a plurality of flexible sections coupled to said frame, said frame and said plurality of flexible sections defining a volume, and at least one injection port for inflating and delating the said volume.

17 Claims, 2 Drawing Sheets

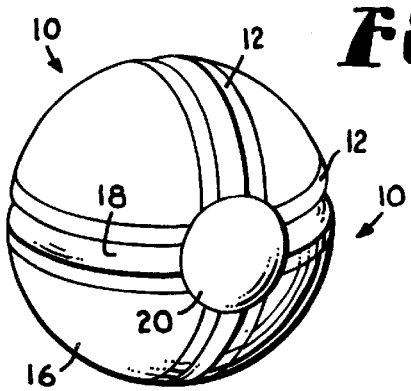
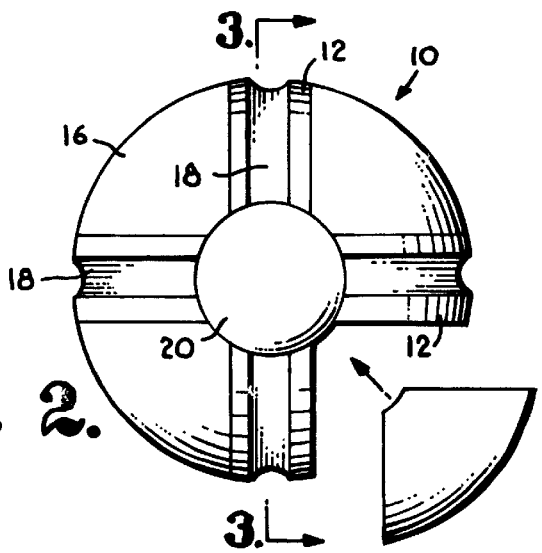
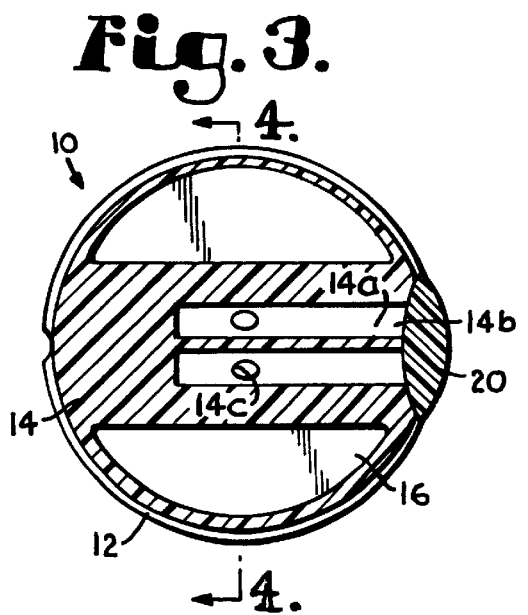
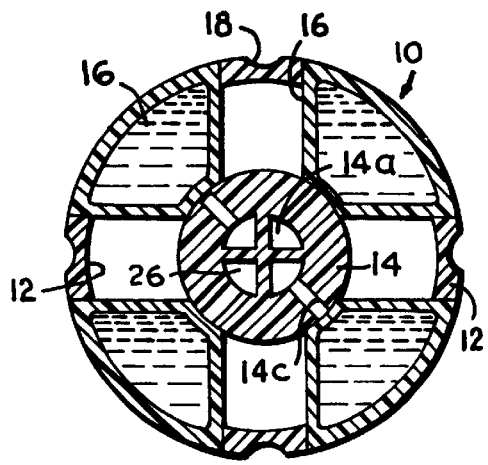
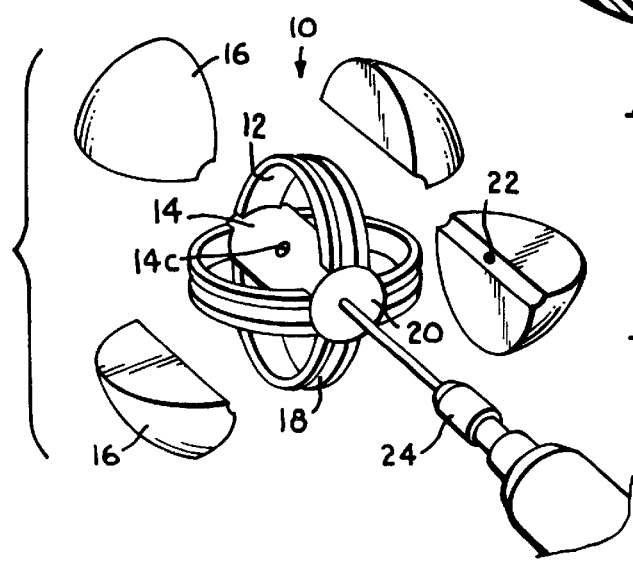

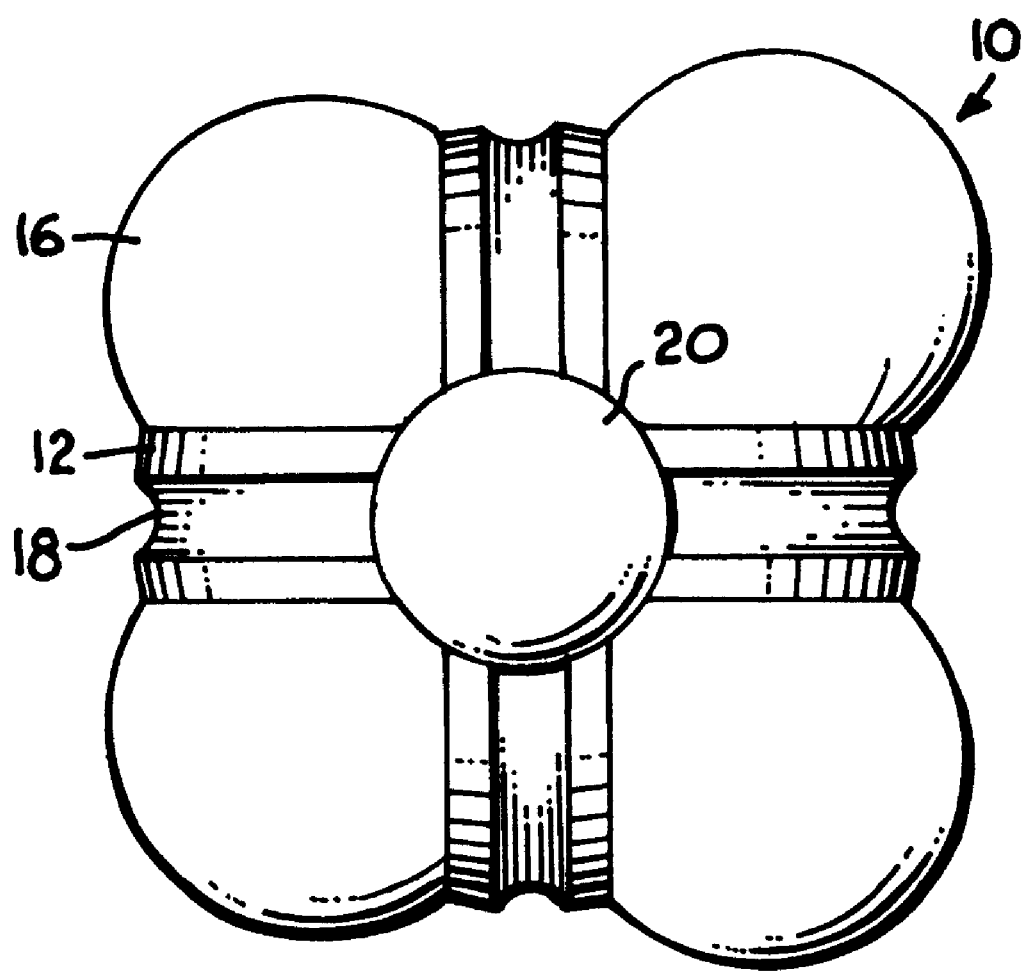

ORBITAL IMPLANT DEVICE

BACKGROUND OF THE INVENTION

The present invention relates generally to an orbital implant device for eye replacement after enucleation and, more particularly, to an adjustable orbital implant device for conforming to an eye socket.

Enucleation is the removal of the globe from the eye socket. The most common indications for enucleation are intraocular malignancy, blind painful eye, prevention of sympathetic ophthalmia and trauma. The enucleation procedure involves the separation of all connections between the globe and the patient so that the globe can be removed.

Implants are used to replace the volume lost by the enucleation procedure. There are two major types of buried implants. The first and most simple are the nonintegrated implants. These implants lack any structure for attachment to the extraocular muscles and do not allow for ingrowth of organic tissue. This type of implant is typically formed of glass, rubber, silicone, steel, gold, silver, polymethylmethacrylate, or the like. The second type of implant is the integrated implant. These implants allow attachment of extraocular muscles, tissue ingrowth, and direct attachment of an ocular prosthesis.

While enucleation can be performed without implant placement, this is not preferred for several reasons. For example, if the volume is not replaced, the enucleation will result in a poor cosmetic result. This will only increase the psychological issues that a patient will have to deal with in this already difficult situation. Therefore, it is recommended that an implant be utilized during the enucleation procedure.

When a prosthesis is going to be used after an enucleation, it is important to have a well-fitting implant. Many problems associated with the use of an implant are caused by inadequate volume replacement. Therefore, an adjustable orbital implant is desirous.

One type of orbital implant utilizes a single balloon attached at a rear portion of an orbital implant. The balloon can then be inflated to increase the surface area of the implant. However, this implant only allows for an increase of the surface area of the implant at one point on the implant. Additionally, this implant does not allow for differential expansile qualities at various points on the implant. Furthermore, by using a single balloon to increase the surface area of the implant, the rectus muscles will also become stretched when the balloon is inflated.

Therefore, an orbital implant device is needed that will allow surface area adjustments at multiple points on the implant without stretching the rectus muscles and that will accommodate differential expansile qualities at various locations on the orbital implant device.

SUMMARY OF THE INVENTION

It is an object of the present invention to provide an orbital implant device that allows expansion of the surface area of the device at more than one point.

It is an object of the present invention to provide an orbital implant device that allows for differential expansile qualities at various positions on the device.

It is a further object of the invention to provide an orbital implant device that allows for the attachment of rectus muscles thereto without significant stretching of the rectus muscles when the surface area of the device is increased.

It is a further object of the present invention to allow an increase or a decrease in the size of the orbital implant through the addition or removal of a fluid media.

In accordance with these and other objects, advantages and novel features of the invention evident from the following description of the preferred embodiment of the invention, an adjustable orbital implant is provided having an outer surface comprising a sphere-defining frame presenting a plurality of openings, a plurality of flexible sections received within said plurality of openings, coupled with said frame, and at least one injection port for the addition and withdrawal of an amount of a fluid media in at least one of said plurality of flexible sections, whereby said flexible sections can be expanded and contracted to vary the size of the orbital implant.

By providing an orbital implant device in accordance with the present invention, numerous advantages are realized. For example, the orbital implant device of the present invention allows for differential expansile qualities at various positions on the orbital implant device. By employing the properties of differential expansile qualities, a doctor will have substantially more control over the shape and size of the orbital implant such that they will be able to conform the orbital implant to fit precisely within the volume created by the enucleation procedure. In addition, the doctor will be able to expand or contract the size of the orbital implant throughout the life of the orbital implant, thereby eliminating the need for replacement of an implant that no longer conforms to a patient's eye socket.

Another feature of the present invention resides in the orbital implant's ability to be expanded and contracted at various points over most of the surface of the device without stretching the rectus muscles. Specifically, this device permits the attachment of the rectus muscles to the orbital implant while allowing for expansion and/or contraction of the orbital implant without readjustment of the rectus muscles because they are attached to a portion of the device that remains static during expansion and contraction.

BRIEF DESCRIPTION OF THE SEVERAL VIEWS OF THE DRAWING

A preferred embodiment of the present invention is described in detail in the accompanying drawings, which form part of the specification, and are to be read in conjunction therewith, and in which like reference numerals are used to indicate like parts in the various views:

FIG. 1 is a perspective view of an orbital implant device of the present invention;

FIG. 2 is a partial exploded view of an orbital implant device of the present invention;

FIG. 3 is a cross-sectional view taken across line 3 of FIG. 2;

FIG. 4 is a cross-sectional view taken across line 4 of FIG.3;

FIG. 5 is a perspective view of the implant device of the present invention after differential expansion; and FIG. 6 is an exploded view of an orbital implant device of the present invention.

DETAILED DESCRIPTION OF THE INVENTION

Referring generally to FIGS. 1 and 2, an orbital implant device employing the principles of the present invention is broadly designated in the drawings and is indicated by reference numeral 10. The preferred embodiment of the present invention includes a frame comprising first and second arcuate bands 12, and a central support member 14. The first and second arcuate bands 12 define a plurality of openings on the surface of the orbital implant device 10. As can be seen in FIG. 1, these openings are substantially covered or filled by four independent expandable quadrant sections 16. As is consistent with the present invention, the orbital implant 10 is designed to fill the void created by enucleation.

More specifically, the frame comprises a first arcuate band 12 extending approximately 360 degrees around a central point, and a second arcuate band 12, also extending around the same point approximately 360 degrees, the first band being removed approximately 90 degrees from the second arcuate band so that the bands extend in substantially perpendicular planes to define a hollow sphere shape divided into four approximately equal quadrants. Each band 12 includes a groove 18 on an outer surface positioned at approximately the midpoint of the band and extending approximately the length of the bands 12. The bands 12 are integral with the central support member 14. The support member extends through the center of the hollow sphere defined by the bands and is coupled at each end to bands 12. The support member is cylindrical in shape and includes a bore 14a which extends inwardly from an open end 14b. The central support member defines four passages 14c extending radially from bore 14a through an exterior surface of the support member. Each of the four passages 14c are separated by a baffle 26. The passages are located in a circular pattern and spaced approximately 90 degrees from one another. The open end of bore 14a is coupled to a self-sealing membrane 20 which is adhesively secured to the central support member 14. The self-sealing membrane has an arcuate outer surface that protrudes beyond the surface of the sphere defined by bands 12.

Quadrant sections 16 have an arcuate upper surface and a concave lower surface connected by two planer side walls. The upper surface area is shaped to cover the exposed quadrant section defined by the arcuate bands 12. The side walls extend inward from the upper surface and taper toward the lower concave surface. The concave lower surface is coupled to the outer surface of the central support member 14. The concave lower surface defines a centrally located opening 22 that extends into a fluid tight volume defined by the upper surface, the lower surface and the side walls of the quadrant sections 16. The openings in quadrant sections 16 are aligned with and in fluid communication with passages 14c located on the central support member 14. Each one of quadrant sections 16 can have different expansile qualities.

In use, an orbital implant device 10 of the present invention is selected by the doctor that will substantially fill the volume remaining after an enucleation procedure. As discussed above, the frame of the device comprises the first and second arcuate bands 12 supported by the central support member 14. In the preferred embodiment, these frame pieces are formed of a flexible material having memory characteristics that allow the device to be deformed to the extent necessary to allow insertion into the void remaining after enucleation. While the frame material is deformable by the doctor for insertion, after it has regained its original shape within the eye socket, it is not deformable under the normal pressures exerted within the socket. The frame can thus be formed of any type of material that is safe for use within the human body and that is either rigid or deformable with memory characteristics. Specifically, the memory characteristics allow the deformed frame to return to its original shape after insertion into the eye socket. The frame can be formed of any approved substance. Preferably, the frame can be formed of silicone or polymethylmethacrylate. However, the frame can also be formed of any rigid porous material such as hydroxyapatite or MEDPOR®.

After the doctor has placed it into the eye socket, he/she will either wait until the frame has regained its original shape or partially inflate the device. After the device has regained its original shape, the doctor will couple the rectus muscles to the device in the grooves 18 on the arcuate bands 12. This is accomplished by tying the rectus muscles around the orbital implant in grooves 18. As discussed above, the pressure exerted on the arcuate bands 12 by the rectus muscles is insufficient to deform the shape of the frame. By attaching the rectus muscles around or directly to the orbital implant, the implant is allowed to move in a fashion similar to a normally functioning eyeball.

After the attachment of the rectus muscles to the orbital implant device, the size of the orbital implant is adjusted to secure the device into the desired volume remaining after the enucleation procedure. The size or surface area of the device can be adjusted through use of the expandable quadrant sections 16 which are formed of a flexible material. The flexible material can be any material that is flexible and safe for use in the human body. In the preferred embodiment, the expandable quadrant sections 16 are formed of silicone. In the preferred embodiment the quadrant sections are puncture resistant. To expand the surface area of the device, a fluid media is used to fill the expandable quadrant sections. The fluid media can be any gas or liquid that is safe for use in the human body. It is preferred that the fluid media be lighter than tissue so that the implant can more freely move within the eye socket. While the media can be either a gas or a liquid, in the preferred embodiment, the media utilized is saline solution.

To expand the surface area of the device by filling sections 16 with the fluid media, the doctor will insert a first needle through the self-sealing membrane 20 into the bore 14a. In the preferred embodiment, the self-sealing membrane 20 protrudes beyond the sphere defined by the bands 12 such that the doctor can palpate the implant to find the membrane 20. This reduces the chances of accidentally puncturing one of the quadrant sections 16. One skilled in the art will appreciate that other structures can be utilized for locating the self-sealing membrane 20. The needle will allow pressure to escape the device as the fluid media is added. The doctor will then insert a second needle of a syringe and needle apparatus 24 which contains the media to be inserted into the device. As best illustrated in FIGS. 3, 4 and 6, when the syringe 24 is depressed by the doctor, the media travels through the self-sealing membrane 20 into the bore 14a defined by the central support member 14. The media then moves through the passages 14c into the expandable quadrant sections 16. The media is forced into the sections 16, they expand to increase the surface area of the device. This expansion fills the volume remaining after the enucleation procedure. When the device is expanded to the appropriate size, the doctor will remove the first needle and then the second needle attached to the syringe 24. Because the membrane 20 is self-sealing, when the needles are removed the device will maintain the expanded size.

In certain circumstances the doctor may determine that the expandable quadrant sections 16 may need to be of varying sizes. As best seen in FIG. 5, the present invention allows the doctor to select sections 16 with different expansile qualities. These different expansile qualities can be achieved by selecting sections 16 formed of different thicknesses. Additionally, not only can the thickness of the sections 16 be changed at each one of the four positions on the device, but the sections 16 can be formed of different materials. Thus, the device can preferentially expand to a greater size in a given direction than in the other remaining directions. This gives the doctor more control for ensuring that the device expands properly within the volume of a patient's eye socket. In addition to changing the expansile qualities of the individual quadrant sections to regulate their size, the central support member 14 can be designed to include a baffle 26 so that the doctor can selectively add a fluid media to each quadrant section independently of the remaining quadrant section. The baffle 26 defines a passageway for directing the fluid media into individual quadrant sections.

In a second embodiment, the expandable quadrant sections 16 are formed of a planar flexible material coupled to the first and second arcuate bands 12. This embodiment functions in the same way as the previous embodiment in that the doctor will insert a first needle through the self-sealing membrane 20 into the bore 14a. This needle will allow air to escape the device as the media is added. The doctor will then insert a second needle that is attached to a syringe 24 containing the media to be inserted into the device. When the syringe is depressed by the doctor, the media travels through the self-sealing membrane 20 into the bore 14a defined by the central support member 14. The media then moves through the passages 14c into a sealed space defined by the planar flexible material and the first and second arcuate bands 12. As the media is forced into the sections 16, the sections 16 expand to increase the surface area of the device to fill the volume remaining after the enucleation procedure. When the device is inflated to the appropriate size, the doctor will remove the first needle and then the second needle. Because the membrane 20 is self-sealing, when the needles are removed the device will maintain the size selected by the doctor. This embodiment also allows the doctor to control the size of each the four sections by selecting the thickness of the planar material used or the type of material used for each section.

While the above procedures describe the addition of a media into the device, it is envisioned that there will be instances when the media will need to be removed from the device. For example, if the device needs to be removed, a doctor will simply insert a needle through the membrane 20 and remove an amount of media necessary for removal of the device.

In addition to the above-described device, the present invention includes a method of utilizing the device. Specifically, the method includes providing an adjustable orbital implant device consistent with the present invention. The device is then collapsed so that the device will fit into a void remaining after an enucleation procedure. After the device has been inserted and has regained its original shape within the void, the rectus muscles are coupled to the device. The size of the device is than adjusted to conform to the individual patient's eye socket.

The process of expanding and contracting the orbital implant, as described above, can be performed throughout the life of the orbital implant. This is important because oftentimes atrophy takes place in the eye socket over time. As the atrophy decreases the size of the eye socket, a doctor can increase the size of the device as outlined above. This avoids having to replace the device due to atrophy. In addition to atrophy, this device is useful for children because, as they grow and the eye socket grows, the size of the device can be increased to fill the eye socket without replacement.

Although the invention has been described with reference to the preferred embodiment illustrated in the drawing figures, it is understood that equivalence may be employed and substitutions made therein without departing from the scope of the invention as recited in the claims.

From the foregoing, it has been seen that this invention is one well-adapted to attain all of the ends and objects hereinabove set forth together with other advantages which are obvious and which are inherent to the structure of the present invention. It will be understood that certain features and subcombinations are of utility and may be employed without reference to other features and subcombinations. This is contemplated by and is within the scope of the claims.

It is further understood that all matter herein set forth or shown in the accompanying drawings is to be interpreted as illustrative and not in a limiting sense.

I claim:

1. An adjustable orbital implant having an outer surface, said implant comprising:
   a sphere defining frame presenting a plurality of openings;
   a plurality of flexible sections coupled with said frame, said frame and said plurality of flexible sections defining an enclosed volume; and
   at least one injection port for adding and removing an amount of a fluid media from said enclosed volume,
   whereby said plurality of flexible sections can be expanded and contracted to vary the size of the orbital implant.

2. An adjustable orbital implant as claimed in claim 1 wherein said plurality of flexible sections covers a substantial portion of said outer surface of said implant.

3. An adjustable orbital implant as claimed in claim 1 wherein said plurality of flexible sections individually define an enclosed cavity having an outer arcuate surface, a pair of side walls and a concave inner surface.

4. An adjustable orbital implant as claimed in claim 3 wherein said frame is formed of two perpendicular arcuate bands supported by a central support member.

5. An adjustable orbital implant as claimed in claim 4 wherein said central support member defines a baffle defining at least one passageway for directing said fluid media to at least one of said plurality of flexible sections.

6. An adjustable orbital implant as claimed in claim 4 wherein said plurality of flexible sections are fixed to said frame at said center member.

7. An adjustable orbital implant as claimed in claim 4 wherein said arcuate bands further define a channel adapted for receipt of rectus muscles.

8. An adjustable orbital implant as claimed in claim 4 wherein said at least one injection port adjusts an amount of a fluid in each of said plurality of flexible sections.

9. An adjustable orbital implant as claimed in claim 4 wherein said at least one injection port is located on said central support member.

10. An adjustable orbital implant as claimed in claim 9 wherein said at least one injection port is self-sealing.

11. An adjustable orbital implant as claimed in claim 1 wherein the number of openings and the number of flexible sections is four.

12. An adjustable orbital implant as claimed in claim 1 wherein at least one of said plurality of flexible sections has a differential expansile quality than any other one of said plurality of flexible sections.

13. An adjustable orbital implant as claimed in claim 1 wherein said frame is selectively collapsible.

14. An adjustable orbital implant for attachment to the rectus muscles comprising:
   a collapsible frame having two perpendicular arcuate bands supported by a center member, said frame defining a hollow and further defining a plurality of openings, said arcuate bands further defining a channel adapted for receipt of said rectus muscles;

a plurality of flexible sections received within said plurality of openings and coupled to said frame at said center member; and an injection port located on said center member for moving a fluid into and out of said plurality of flexible sections, whereby said sections can be expanded and contracted to vary the size of said implant.

15. An adjustable orbital implant as claimed in claim 14 wherein said plurality of flexible sections totals four.

16. An adjustable orbital implant as claimed in claim 14 wherein said center member defines a channel for movement of said fluid from said injection port to said plurality of flexible sections.

17. A method of attaching an orbital implant into an eye socket with the rectus muscles wherein the size of the orbital implant is adjustable, comprising:

providing an adjustable orbital implant having a sphere defining frame presenting a plurality of openings, a plurality of flexible sections coupled with said frame, said flexible sections can be expanded and contracted to vary the size of said implant, said frame and said flexible sections can be expanded and contracted to vary the size of said implant, said plurality of flexible sections defining a volume and at least one injection port for adding and removing an amount of a fluid media from said volume;

collapsing said implant;

inserting said implant into an eye socket;

coupling the rectus muscles around said orbital implant; and adjusting the size of said plurality of flexible sections to conform the orbital implant to the eye socket.

\* \* \* \* \*

UNITED STATES PATENT AND TRADEMARK OFFICE
CERTIFICATE OF CORRECTION

PATENT NO. : 6,419,698 B1
DATED : July 16, 2002
INVENTOR(S) : Paul T. Finger

It is certified that error appears in the above-identified patent and that said Letters Patent is hereby corrected as shown below:

Title page,
Item [56], References Cited, U.S. PATENT DOCUMENTS, insert
-- 4,332,039, 6/1982, LaFuente;
5,026,392, 6/1991, Gordon;
5,192,315, 3/1993, Jacob-LaBarre;
5,466,258, 11/1995, Rubin;
5,584,880, 12/1996, Martinez --.

FOREIGN PATENT DOCUMENTS, insert
-- JP, JP406217999, 8/1994 --.

OTHER DOCUMENTS, insert
-- Darius M. Moshfeghi, MD, et al., "Enucleation," Survey of Ophthalmology, Vol. 44, No. 4, January - February 2000, pp. 277-301 --.

Signed and Sealed this

Second Day of December, 2003

JAMES E. ROGAN
*Director of the United States Patent and Trademark Office*